(12) United States Patent
Cedgard

(10) Patent No.: US 7,022,338 B1
(45) Date of Patent: Apr. 4, 2006

(54) TABLETS COMPRISING MICRO-ORGANISMS AND METHOD FOR PREPARATION OF THE TABLETS

(75) Inventor: Lennart Cedgard, Göteborg (SE)

(73) Assignee: Wasa Medicals AB, Gothenburg (SE)

( * ) Notice: Subject to any disclaimer, the term of this patent is extended or adjusted under 35 U.S.C. 154(b) by 453 days.

(21) Appl. No.: 10/148,071

(22) PCT Filed: Nov. 24, 2000

(86) PCT No.: PCT/SE00/02327

§ 371 (c)(1),
(2), (4) Date: Sep. 26, 2002

(87) PCT Pub. No.: WO01/37880

PCT Pub. Date: May 31, 2001

(30) Foreign Application Priority Data

Nov. 25, 1999 (SE) .................................... 9904297
Apr. 19, 2000 (SE) .................................... 0001447

(51) Int. Cl.
*A61K 9/20* (2006.01)

(52) U.S. Cl. ...................... 424/465; 424/464; 514/777; 514/782

(58) Field of Classification Search ................ 424/464, 424/465, 439
See application file for complete search history.

(56) References Cited

U.S. PATENT DOCUMENTS 4,888,171 A * 12/1989 Okonogi et al. ........... 424/93.4
5,427,799 A    6/1995 Valentine et al.
6,451,344 B1 * 9/2002 Sotoyama et al. ........... 424/479
6,461,607 B1 * 10/2002 Farmer .................... 424/93.45

FOREIGN PATENT DOCUMENTS

EP    0 931 543 A1    7/1999
WO    WO 97/07822    3/1997

* cited by examiner

*Primary Examiner*—James M. Spear
(74) *Attorney, Agent, or Firm*—Albihns Stockholm AB

(57) ABSTRACT

Tablet containing living micro-organisms, produced from a pressed tablet material comprising micro-organisms and oligosaccharides and/or polysaccharides, the tablet material also comprising at least one slime-forming agent. The invention also relates to a process for the production of such a tablet.

9 Claims, 4 Drawing Sheets

TABLETS COMPRISING MICRO-ORGANISMS AND METHOD FOR PREPARATION OF THE TABLETS

CROSS REFERENCE TO RELATED APPLICATIONS

This application is a national stage application of International Application PCT/SE00/02327, filed Nov. 24, 2000, designating the United States of America, which claims the benefit of Swedish Patent Application No. 0001 447-2, filed April 19, 2000 and Swedish Patent Application No. 9904297-0, filed Nov. 25, 1999.

TECHNICAL FIELD

The invention relates to tablets containing micro-organisms and a process for the production thereof. More particularly, the invention relates to tablets containing micro-organisms having high viability.

BACKGROUND ART

Tablets are usually produced by pressing a powdery material in a mould into a suitable shape in a so-called tablet-pressing machine. This process is usually referred to as tabletting. The tablets can be of different shape, size and hardness depending on the properties of the tablet material and the pressure to which they are subjected in the pressing.

When the tablets are produced, heat is generated as a result of friction against the wall surfaces of the mould and internal friction in the tablet material. Since the tablets usually consist of chemicals and the temperature increase is not particularly high, this does not cause any problem since the chemicals tolerate heat well. If, however, the tablets (the tablet material) contain living micro-organisms, such as bacteria, which are sensitive to splintering forces and heat, this leads to a severe reduction in the number of living micro-organisms, i.e. the viability, when the tablets are pressed. For certain known tablet materials, it is not uncommon for the viability in the tablet material to be reduced by up to 90%, or sometimes even more in the course of tabletting.

This problem cannot be avoided by quite simply applying a lower pressure to the conventional tablet material and thereby achieving lower heat generation, since the tablet has to be subjected to a certain minimum pressure in order for the shape to be maintainable.

A solution to this problem is, however, described by virtue of WO-A1-97/07822, which solution entails the tablet material which is pressed containing oligosaccharides, for example inulin, in addition to living micro-organisms. The pressing can consequently be effected at considerably lower pressure, resulting in reduced heat generation and increased viability.

Problem

Nevertheless, there sometimes remains the problem that the dissolution of the tablets is not always wholly satisfactory or does not occur in the ideal region. In a certain type of treatment, for example in treatment of the gastro-intestinal tract, it is vitally important for the tablets to be able to be targeted at the intended region.

SHORT DESCRIPTION OF THE INVENTION

According to the invention, a solution to the abovementioned problems is achieved by the tablet substance containing slime-forming agent, in addition to micro-organisms and saccharides chosen from amongst oligosaccharides and polysaccharides, preferably fructosaccharides.

By "oligosaccharides" are meant saccharides which offer 2–10 molecules of a monosaccharide and by "polysaccharides" are meant those which offer more than 10 molecules of a monosaccharide.

Surprisingly, the admixture of oligosaccharides and/or polysaccharides and slime-forming molecular compounds in tablet-filler material as "support substance" has also proved to facilitate tabletting, which means that the tabletting can be effected with lower compression, whilst at the same time the friability is improved, and that the level of wear and hardness of the tablet are maintained.

According to one preferred embodiment of the invention, a tablet containing living microorganisms is achieved, produced from a pressed tablet material comprising micro-organisms and fructosaccharides, the tablet material also comprising at least one slime-forming agent.

One preferred slime-forming agent is xanthan, or derivatives thereof, and other examples of slime-forming agents are gum tragacanth or gum arabic. Other slime-forming agents are also possible, depending on the field of application.

Expediently, the slime-forming agent is present in a quantity of above 0 up to 10% by weight, based on the whole of the tablet material.

The tablet according to the invention probably has cavities in which living micro-organisms, such as bacterial cultures, are protected. In addition, the disintegration and dissolution of the tablet can easily be regulated by using fructosaccharides of different quality and, at the same time, mixing in different quantities of slime-forming agent.

The tablet can be targeted at an intended region in the gastro-intestinal tract, which results in a regulated dissolution. When the tablet dissolves, the micro-organisms are protected by slime which appears when the slime-forming agent is released. The slime is formed after the dissolution. Moreover, the micro-organisms obtain food for their own development and vitality through the release of the fructosaccharides.

According to one preferred embodiment of the invention, the saccharides are present in a quantity of from 40 to 70% by weight of the tablet material, without the admixture of any other support substance.

The tablets might also contain polysaccharides such as microcrystalline cellulose and starch, as well as other conventional additives.

The invention also relates to a process for the production of the tablets according to the invention, which process comprises the step of pressing tablets out of a substance containing living organisms, oligosaccharides and/or polysaccharides, preferably fructosaccharides, and slime-forming agent.

According to one preferred embodiment of the invention, the process comprises the following steps:

pressing a tablet material comprising micro-organisms and oligosaccharides and/or polysaccharides, preferably fructosaccharides, at a reduced pressure compared with conventional tabletting processes not involving oligosaccharides and/or polysaccharides, the tablet material being mixed, prior to pressing, with at least one slime-forming agent, for example xanthan or derivatives thereof, gum tragacanth or gum arabic.

The tablets according to the invention have increased viability in respect of the bacterial cultures used, equivalent to a factor of 5-10 compared with conventional tablet-filler material and processes.

The striking pressure in tabletting can be reduced by up to 90% compared with conventional tabletting processes, combined with maintained friability of less than 1.0 (approved reference values according to GMP in pharmaceuticals production are 0.1–1.0). The splintering forces are substantially reduced, which means that the bacteria are not destroyed to the same degree as with conventional methods.

The tablets are also easy to swallow, owing to the fact that slime is formed already in the mouth.

The invention will now be described in greater detail with reference to the accompanying figures.

SHORT DESCRIPTION OF FIGURES

Figure 5A:
Figure 5B:

FIGS. 5a–b show the structure of the matrix in a tablet according to one embodiment of the invention.

Figure 6:
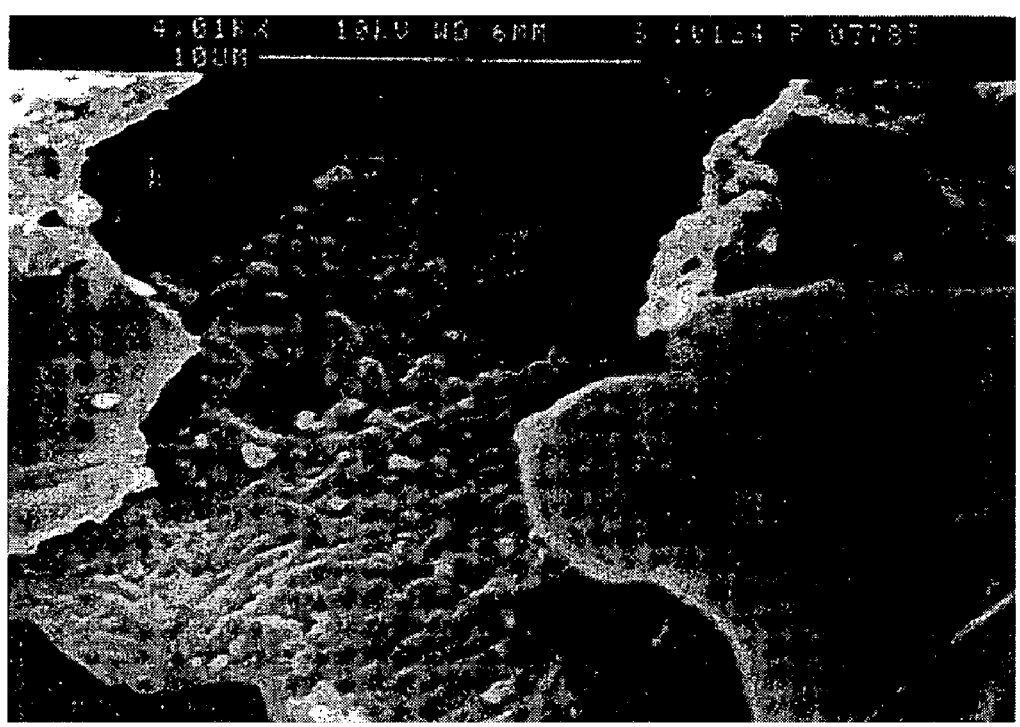

FIG. 6 shows a zoom-in on the tablet.

DETAILED DESCRIPTION OF THE INVENTION

The tablets according to the invention comprise living micro-organisms, for example lactic-acid-producing cultures, known as probiotica, which are intended to normalize or balance the bacterial flora in the gastrointestinal tract. Examples of micro-organisms are Streptococcus thermophilus, Lactobacillus bulgaricus and Bifidobacterium lactis.

Through the admixture of oligosaccharides and/or polysaccharides, preferably fructosaccharides, in the tablet substance, a substance is obtained which enables the tablets to be pressed at lower pressure, in which case the splintering forces are reduced and less heat is generated, whilst the hardness of the tablets is maintained.

The quantity of saccharides is dependent on various crystalline properties, but is expediently above 40% by weight of the total mass of the tablet. A lower saccharides admixture level leads to a smaller differential in terms of viability compared with conventional methods. Inulin can be used, for example, which has previously been known to constitute food for probiotica cultures, more particularly, in this case, bifidobacteria.

No other support substances need to be added, but the invention is not limited to the use of oligosaccharides alone. For example, calcium diphosphate, microcrystalline cellulose and starch can be added in a suitable, preferably small quantity above zero.

The bacterial cultures can be mixed in, for example, at between 0.1% and 30% of the total final tablet mass.

The brittleness of the tablet, i.e. the friability, is not altered in the tablet substance according to the invention. This will be less than 1.0, which can be compared with reference values which are accepted according to GMP (Good Manufacturing Practice). The friability is quoted in percent weight reduction for the tablets when they are rotated 100 revolutions in a standard test device, which will not be described in greater detail since it is well known within the field.

The invention will be described in greater detail below with reference to two examples, of which Example 1 describes a process (tablet) according to the invention and Example 2, which is a comparative example, describes a conventional process (tablet).

EXAMPLES

Example 1

Content of the tablet substance according to one embodiment of the invention

| | |
|---|---|
| Str. *thermophilus* & *Lactobacillus bulgaricus* | 2.5% |
| *Bifidobacterium lactis* | 2.5% |
| | 5% |
| Xanthan | 2.0% |
| Magnesium stearate | 0.5% |

Inulin and other substances constitute the remainder.

Tablets were produced with a tabletting process which is conventional per se and is not described in greater detail, but at reduced pressure, the compression having been 200 kP (corresponding to a 90% pressure reduction). Friability was 0.31 and hardness 2.75 kP.

This resulted in the number of colony-forming units before tabletting, which was 5E9, having been reduced to 4E9 after. The reduction thus amounted to 20%.

Example 2 (Comparative Example)

Str. thermophilus & Lactobacillus bulgaricus

Bifidobacterium lactis

Calcium diphosphate

Microcrystalline cellulose

Friability was 0.31 and hardness 4.5 kP.

Tablets were produced in the same way as in Example 1, but at higher pressure (2000 kP).

This resulted in the number of colony-forming units before tabletting, which was 5E9, being reduced to 3E8 after. The reduction thus amounted to 94%.

Various tests which were conducted on the produced tablets are described below, the various tests having been classified under their respective headings.

Light Microscopy:

Tablets were subsequently crushed into parts and dissolved in 0.9% NaCl, one tablet per 5 ml solution, for ca. 2 hours under constant stirring. The solution was slightly turbid.

The bacteria were coloured with "acridine orange", 0.1% in 0.9% NaCl, for 1 minute. The excess solution was removed with a filter paper and the substance covered with a cover strip. The substance was examined with light microscopy (LM) by means of fluorescence.

"Confocal Laser Scanning Microscopy":

Tablet parts were coloured with "acridine orange" for one minute and mounted on a slide for a microscope. The solution penetrated the tablets and the bacteria were coloured. The tablets were then examined by means of "Confocal Laser Scanning Microscopy".

Scanning Electron Microscope (SEM):

Tablets were crushed and mounted on "SEM plates" with an electrically conductive glue. The surface was coated with gold.

Figure 1:
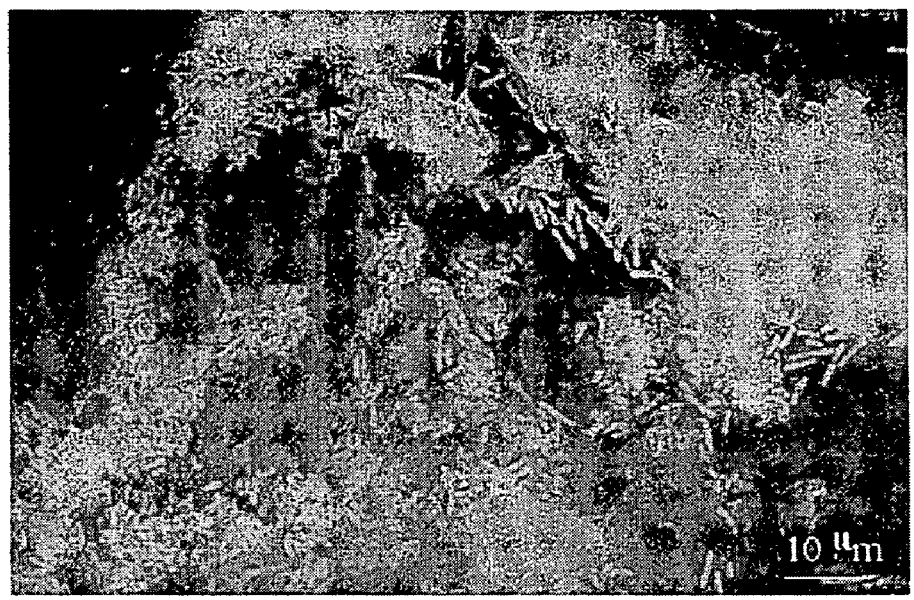
FIG. 1 shows bacteria in a tablet according to the invention.
Figures 2A, 2B:
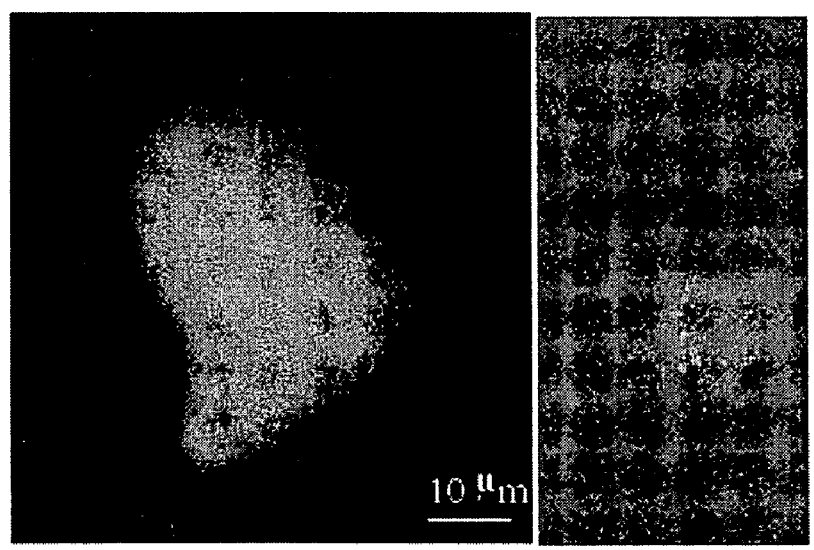
FIG. 2 shows bacteria in a reference tablet.

The results can be seen from FIGS. 1 and 2. FIG. 1 corresponds to a tablet material according to one embodiment of the invention and FIG. 2 corresponds to a reference material with content according to Example 2. FIGS. 1 and 2 shows the result after light microscopy.

FIG. 1 shows that bacteria were easily found in the tablet according to the invention and appeared to have been preserved.

In the reference tablet shown in FIG. 2, it was difficult to find well-preserved bacteria when this test was used. Relatively large areas of the bacteria were found, but the cells appeared to have been destroyed and it was difficult to identify individual bacteria. Only small groups of bacteria were found.

Figure 3:
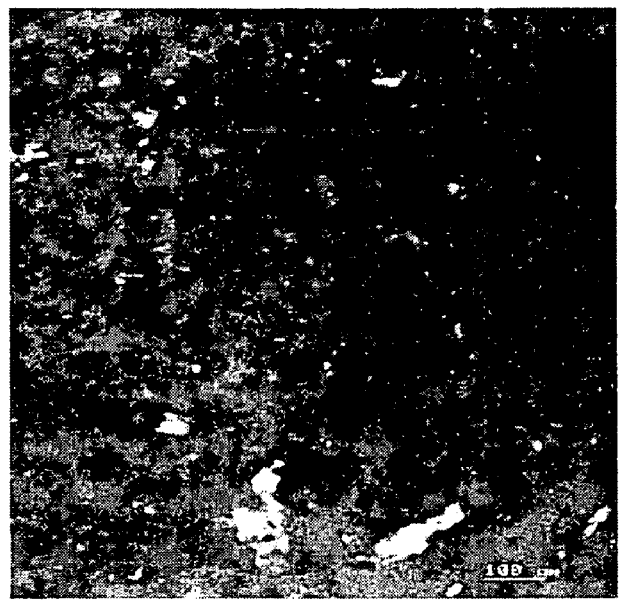
FIG. 3 shows how the structure in a tablet according to one embodiment of the invention looks in enlargement. The structure has porosities in which bacteria can collect.

FIG. 3 shows how the structure in a tablet according to one embodiment of the invention looks in enlargement. The structure has porosities in which bacteria can collect.

Figure 4:
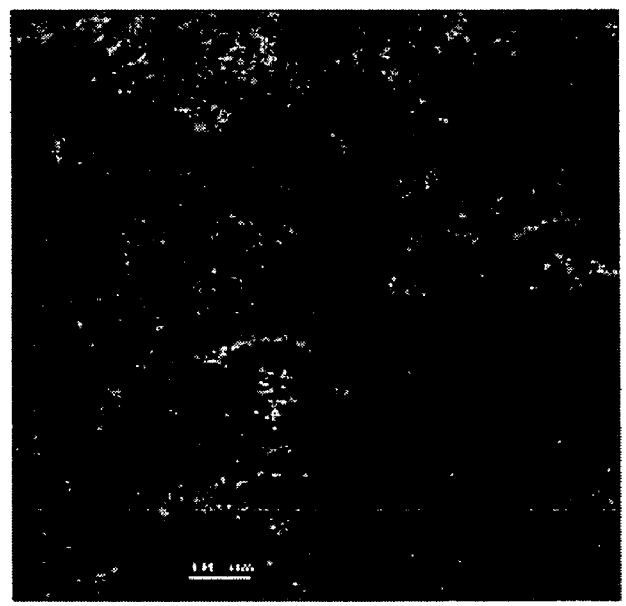
FIG. 4 shows the dominant structure in a tablet according to one embodiment of the invention.

FIG. 4 shows the dominant structure in a tablet according to one embodiment of the invention. The particles which contain bacteria are often spherical. The bacteria are presumably well protected in cavities.

FIGS. 5*a*–b show the structure of the matrix in a tablet according to one embodiment of the invention.

FIG. 6 shows a zoom-in on the tablet.

The other tests show corresponding results, which means that the tablets according to the invention exhibited an increase in maintained viability after tabletting of up to 1000% compared with conventional tablet materials, owing to the presence of a slime-forming agent, which agent also brings further advantages, such as that disintegration and dissolution can easily be regulated.

The invention is not limited to the preferred embodiments shown but can be modified within the scope of the patent claims.

What is claimed is:

1. Tablet containing living micro-organisms, produced from a pressed tablet material comprising:
   micro-organisms;
   oligosaccharides and/or polysaccharides ;and
   at least one slime-forming agent, wherein
   said slime-forming agent is selected from the group consisting of xanthan, xanthan derivatives, gum tragacanth and gum Arabic; and
   said slime-forming agent is present in a quantity of above 0 up to 10% by weight, based on the whole of the tablet material.

2. Tablet according to claim 1, characterized in that the saccharides are present in a quantity of upwards of 40% by weight of the tablet material.

3. Tablet according to claim 1, characterized in that the micro-organisms are present in a quantity of from above 0 to 30% by weight of the tablet material.

4. Tablet according to according to claim 1, characterized in that the micro-organisms consist of lactic-acid-producing bacteria.

5. Tablet according to claim 1, characterized in that the saccharides consist of fructosaccharides.

6. Process for the production of tablets containing living micro-organisms, which process comprises the following steps:
   pressing a tablet material comprising micro-organisms and oligosaccharides and/or polysaccharides at a reduced pressure compared with conventional tabletting processes not involving the said saccharides,
   characterized in that the tablet material is mixed, prior to pressing, with at least one slime-forming agent selected from the group consisting of xanthan, xanthan derivatives, gum tragacanth and gum Arabic and said slime-forming agent is present in a quantity of above 0 up to 10% by weight, based on the whole of the tablet material.

7. Tablet according to claim 5, characterized in that the fructosaccharides are inulin.

8. Tablet according to claim 6, characterized in that the oligosaccharides and/or polysaccharides are fructosaccharides.

9. Tablet according to claim 8, characterized in that the fructosaccharides are inulin.

* * * * *